United States Patent [19]

Bucalo

[11] 4,036,214
[45] July 19, 1977

[54] FLUID-COLLECTING AND MICROORGANISM-DETECTING DEVICES

[76] Inventor: Louis Bucalo, 155 Roberts St., Holbrook, N.Y. 11741

[21] Appl. No.: 568,139

[22] Filed: Apr. 14, 1975

[51] Int. Cl.² .................................... A61B 10/00
[52] U.S. Cl. ........................... 128/2 F; 128/2 W; 128/275; 195/139
[58] Field of Search ............ 128/2 F, 2 W, 2 R, 260, 128/275, 1 R; 195/103.5 R, 139, 140

[56] References Cited

U.S. PATENT DOCUMENTS

| | | | |
|---|---|---|---|
| 3,057,344 | 10/1962 | Abella et al. | 128/2 F |
| 3,308,039 | 3/1967 | Nelson | 128/2 W X |
| 3,315,660 | 4/1967 | Abella | 128/2 F |
| 3,485,235 | 12/1969 | Felson | 128/2 F |
| 3,683,890 | 8/1972 | Beal | 128/2 W |
| 3,722,503 | 3/1973 | Hovick | 128/2 F |
| 3,853,116 | 12/1974 | Bucalo | 128/1 R |

Primary Examiner—Kyle L. Howell
Attorney, Agent, or Firm—Steinberg & Blake

[57] ABSTRACT

Devices for collecting body fluids and/or detecting the presence of microorganisms. The device is capable of being introduced into a body cavity and to remain therein, this device having an enclosure provided with a capillary structure which is capable of transferring body fluids with microorganisms therein from the exterior to the interior of the enclosure while the latter remains in a body cavity. A structure is provided for completely closing the enclosure in a fully automatic manner after the body fluids have been transferred into the interior of the enclosure, so that in this way the enclosure can reliably remain for an extended period in the body cavity without any fear that microorganisms in the enclosure will return out of the latter back into the body.

14 Claims, 10 Drawing Figures

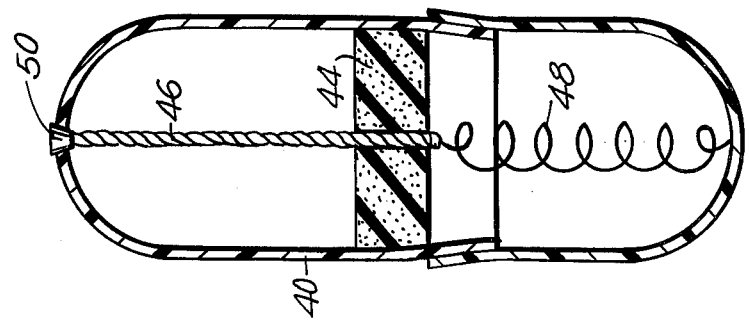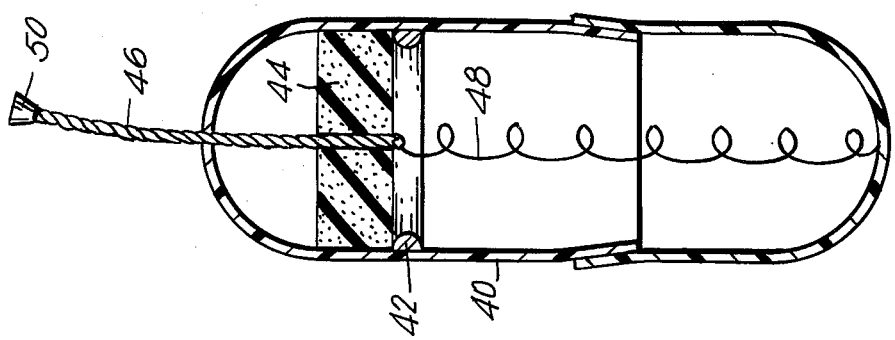

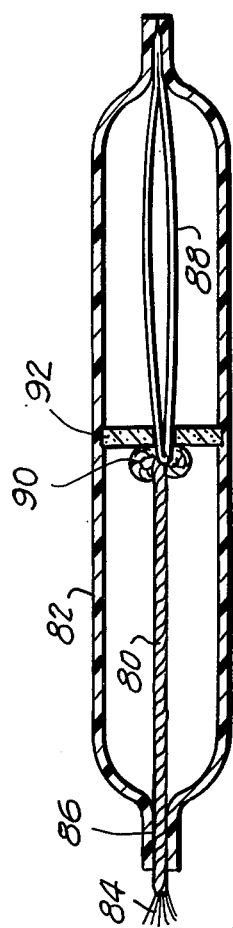
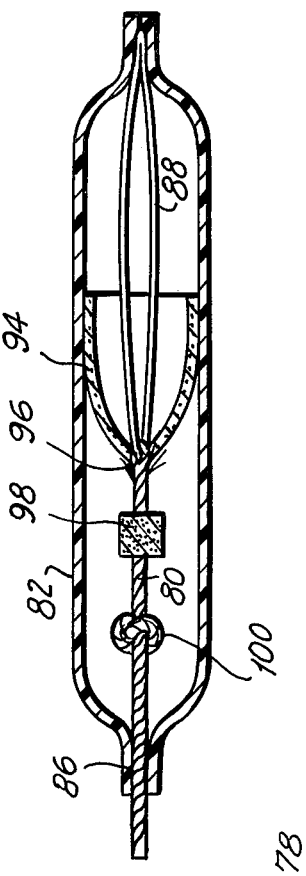
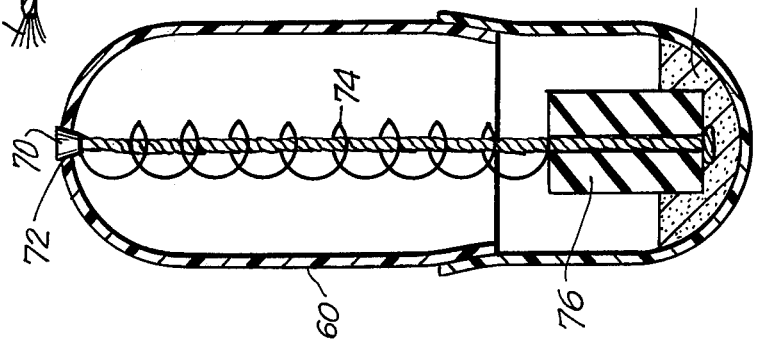
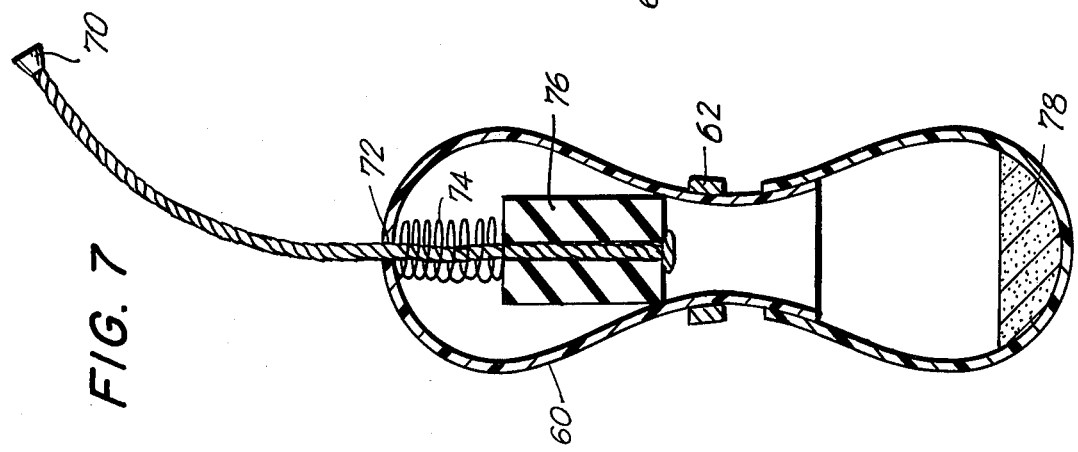

FLUID-COLLECTING AND MICROORGANISM-DETECTING DEVICES

BACKGROUND OF THE INVENTION

As is well known, it is highly desirable to be able to detect in a reliable manner whether or not certain microorganisms are present in body cavities.

Conventionally, the detection of the presence or absence of suspected microorganisms is carried out by way of removing a specimen of a body fluid which is suspected of having certain microorganisms therein from a body cavity to the exterior thereof where the specimen is placed on a suitable growth medium and cultured so as to be able to indicate the presence or absence of microorganisms.

Such procedures are highly unreliable for a number of different reasons such as, for example, the fact that the microorganisms are grown under conditions completely different from those prevailing in the body cavity and also the fact that the microorganisms are transferred through atmospheres which are highly deleterious to the microorganisms so that certain microorganisms will not be capable of reliable growth out of the environment in the body where these microorganisms naturally occur.

In order to avoid drawbacks of the above type it has already been proposed to situate in a body cavity an absorbent medium which will receive body fluids with suspected microorganisms therein for the purpose of placing the microorganisms at least temporarily while in the body cavity in engagement with a suitable nutrient.

However, procedures of this latter type also have inherent drawbacks in that great care must be exercised to make certain that devices of the above type do not remain in the cavity of the body for an excessively long time. In other words one-way travel of the microorganisms to the nutrient must be assured, and the only way to assure such a procedure is to make certain that the device is removed from the body cavity only after a relatively short time during which it is certain that the microorganisms have not had an opportunity to multiply to such an extent that they will have a deleterious effect on the body while the devices remain in the body.

In addition to the above drawback of the necessity of removing the device within a given time interval, there is the drawback resulting from the fact that this time interval may not be sufficient for suitable cultures to be grown directly in the body, so that growth of the cultures must be continued outside of the body, and this latter requirement of course represents certain inconveniences.

Furthermore, even with these devices which remain in the body cavity it is possible to assume that a suitable sample has been absorbed by the device whereas actually a sample has not been taken into the device, so that a false negative indication may result.

Also, with devices of the above type it is often difficult to determine visually whether or not certain microorganisms are present.

SUMMARY OF THE INVENTION

It is accordingly a primary object of the present invention to provide devices which will avoid the above drawbacks.

In particular, it is an object of the present invention to provide a device which can remain for an extended period of time within a body cavity without any danger of having an undesirable effect on the body even though microorganisms are grown in the device while it remains in the body cavity for an extended period.

It is furthermore an object of the present invention to provide a device which can simply be inspected upon being withdrawn from the body cavity to given an indication as to whether or not a sample has indeed been taken into the device.

It is also an object of the present invention to provide a device of the above type which is capable of operating in such a way that the visibility of microorganisms is greatly enhanced.

In addition, it is an object of the present invention to provide devices of the above general type which are characterized by extreme simplicity in their construction and reliability in their operation.

According to the invention the device includes an enclosure which is capable of being introduced into and remaining for an extended period in the interior of a body cavity where the presence of certain microorganisms is suspected. A transfer means extends from the exterior to the interior of the enclosure for transferring to the interior thereof body fluids which may carry the suspected microorganisms. A closure means is provided for completely closing the enclosure in a fully automatic manner only after a time interval during which the transfer means is capable of effectively transferring body fluids from the exterior to the interior of the enclosure, so that after this time interval has elapsed it is possible for microorganisms to be safely retained in the enclosure while the latter remains in the body cavity. Thus, if, for example, a nutrient is situated in the enclosure to grow microorganisms, the enclosure with the nitrient can remain in the body cavity for growing microorganisms under the best possible conditions in the body cavity itself without any danger that the multiplying microorganisms will be capable of escaping from the enclosure back into the body.

BRIEF DESCRIPTION OF DRAWINGS

The invention is illustrated by way of example in the accompanying drawings which form part of this application and in which:

FIG. 1 is a schematic sectional elevation of an embodiment of a device of the invention shown in the condition it has prior to introduction into a body cavity;

FIG. 2 shows the device of FIG. 1 after it has remained in the body cavity for a given interval;

FIG. 7 is a schematic elevation of yet another embodiment of a structure according to the invention shown in the condition it has prior to introduction into a body cavity;

FIG. 8 shows the device of FIG. 7 after it has remained in the body cavity for a given interval;

FIG. 9 is a schematic section elevation of yet another embodiment of a device according to the invention; and FIG. 10 is a schematic section elevation of a still further embodiment of a device according to the invention.

DESCRIPTION OF PREFERRED EMBODIMENTS

Figure 6:
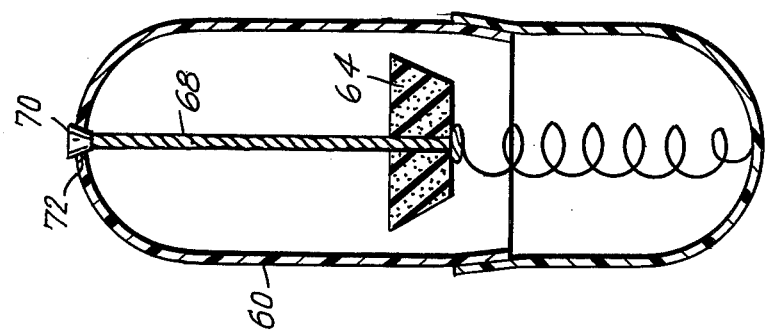
FIG. 6 shows the device of FIG. 5 after it has remained in the body cavity for a given interval.

Referring first to FIG. 1, the device of the present invention which is illustrated therein includes an enclosure 40 in the form of a suitable capsule of generally cylindrical configuration having ends in the forms of hemispheres. The capsule may be made of any suitable plastic initially composed, for example, of a pair of enclosure halves which are sealed together at the central region.

Before these capsule sections are sealed together a dry absorbent matrix 44 is situated in the enclosure 40. This body 44 may be in the form of a sponge.

This top end of the enclosure is formed with an opening through which a transfer means extends. In the example of FIG. 1 the transfer means 46 takes the form of a wick which acts by capillary action. Thus in the initial condition illustrated in FIG. 1 the transfer means 46 extends from the exterior toward the interior of the enclosure 40. The inner part of the wick 46 is fixed to the expandable body 44 preferably at the bottom end thereof with the wick extending through the body 44.

At its outer free end the wick 46 carries a plug 50 which may have the tapered configuration illustrated and which is capable of tightly closing the opening through which the wick extends.

The dry absorbent body 44 is capable of having impregnated or contained therein in any suitable way a suitable nutrient for suspected microorganisms and it also may contain certain antibiotics for making certain that microorganisms in which there are no interest are killed so as not to disturb the viewing of the suspected microorganisms. However, it is to be understood that if desired no nutrients or antibiotics need be located in the body 44 since the absorbed fluids can be treated subsequent to the removal of the device from the body cavity if so desired. It is preferred, however, to grow the microorganisms in the body cavity because the conditions prevailing therein are ideal for this purpose.

In use, this device of FIG. 1 is simply introduced into any body cavity in such a way that the transfer means 46 will contact body fluids in which it is suspected that certain microorganisms are present. These microorganisms will by capillary action flow along the wick 46 into the sponge 44. This sponge will absorb the liquid. When reaching the condition shown in FIG. 2 the plug 50 will seal the opening so that the enclosure 40 is completely and tightly closed in this way. Now the device of FIG. 2 may be permitted to remain in the body cavity for as long as desired so as to assure growth of microorganisms directly in the body cavity.

After the desired time the entire device can be removed from the body cavity in any suitable way and inspected to determine the presence or absence of microorganisms. This inspection may be enhanced by piercing through the wall of the enclosure 40 and introducing into the sponge 44 a suitable dye by way of a suitable syringe, for example, so that with this dye the visibility of suspected microorganisms is greatly enhanced.

It is apparent that with this construction of the invention certain considerable advantages are achieved. In the first place there is no danger that the multiplying microorganisms will have any deleterious effect on the body because the enclosure 40 is tightly closed in a fully automatic manner after an interval, and during this interval it is only possible for microorganisms to move into the enclosure but not out of the same.

Furthermore, if the device is removed and is still in the condition shown in FIG. 1, then it is known that a sample has not been taken so that the device can be reintroduced at a better location. Thus, false negatives are avoided in this way.

Furthermore, the reason why a sample was not transferred by the transfer means 46 may be that the body fluids are highly viscous. Therefore, according to a further feature of the invention it is possible to introduce into the body cavity a suitable diluting solution which will render the body fluids less viscous, and then the device can be reintroduced so that the test procedures can be repeated. The diluting solution may be in the form of a spray which is sprayed into the body cavity so as to render the body fluids less viscous. This diluting solution may, for example, contain a mucolytic agent such as acetylcysteine, mucinases enzymes, or proteolytic enzymes.

Of course, when the device of FIG. 1 is used without a nutrient, then after the device has the condition of FIG. 2, the body fluid captured by the body 44 as well as by the wick 46 can be tested at the outside of the body for the presence or absence of microorganisms.

Also, it is possible to situate in the interior of the enclosure a suitable preservative for the collected body fluid. For example where the collected body fluid is blood, a preservative in the form of a citric acid may be used.

According to the embodiment of the invention which is illustrated in FIG. 1 the enclosure 40 has in its interior a ring 42 of a material which will dissolve when contacted by a body fluid. This dissolvable or meltable retainer ring forms an automatic trigger mechanism together with the dry absorbant matrix 44 which may or may not have a nutrient therein. The wick 46 extends through the matrix 44 while being connected to one end of a tensioned springy member 48 the opposite end of which is fixed to the bottom end of the enclosure 40, as viewed in FIG. 1. Thus, the spring 48, which may be a rubber band instead of a coil spring, can be attached as by a suitable adhesive to the bottom end of the enclosure and it can be connected with a suitable knot, for example, to the inner end of the wick 46 which carries closure plug 50.

Thus, when this embodiment is used it is simply introduced into the body cavity so that a body fluid will be transferred by the transfer means 46 from the exterior to the interior of the enclosure 42. The liquid will be absorbed by the matrix 46 which need not necessarily expand since this liquid will flow through the matrix 46 to the trigger retaining ring 42 which melts or dissolves upon being engaged by the body fluid so as to release the wick 46 to the force of the tension spring 48. After a time sufficient for the trigger ring 42 to dissolve or melt has elapsed, the spring 48 will contract upon itself to assume the condition shown in FIG. 2 pulling the transfer means 46 into the enclosure while tightly closing the latter with the plug 50 so as to achieve the results set forth above.

Figure 3:
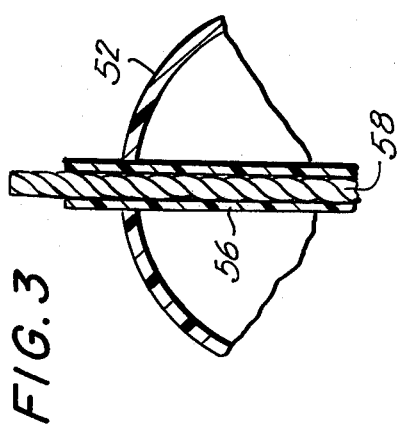
FIG. 3 is a fragmentary partly sectional schematic elevation of another embodiment prior to introduction into a body cavity.
Figure 4:
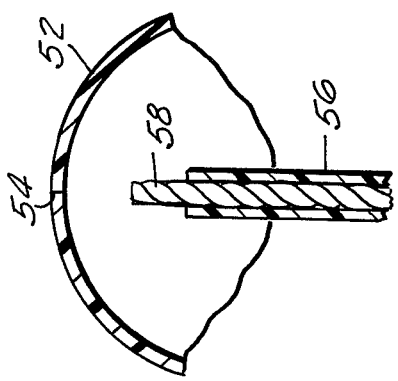
FIG. 4 shows the device of FIG. 3 after it has remained in the body cavity for a given interval.

The embodiment of the invention which is illustrated in FIGS. 3 and 4 may be identical with those described above except that in this case the end 52 of the enclosure through which the transfer means extends is formed with a simple slit 54 while the wall of the capsule 52 is made of a springy material which tends to tightly close this slit 54 upon itself. However, initially a plastic tube 56 with a wick 58 therein extends through the slit in the dry condition shown in FIG. 3. Thus, with this embodiment in response to transfer of fluid to the interior of the enclosure, this fluid will act in the manner described above in connection with FIGS. 1 or 2 to retract the plastic tube 56 and 58 into the interior of the enclosure. Thus, this construction of FIGS. 3 and 4 may be used with a spring and trigger release as shown on FIGS. 1 and 2.

However, with this embodiment the tube and wick are drawn completely into the interior of the enclosure as shown in FIG. 4 so that the slit 54 closes upon itself for providing the tight closure.

Figure 5:
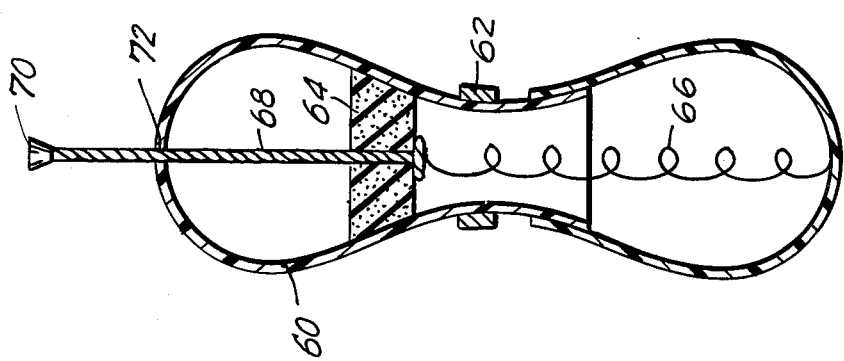
FIG. 5 is a schematic section elevation of a further embodiment of a device according to the invention as shown in the condition it has prior to introduction into a body cavity.

The embodiment of the invention which is illustrated in FIGS. 5 and 6 includes a flexible enclosure 60 which initially is compressed at an intermediate region by a body 62 made of any suitable material which is capable of dissolving or melting in response to conditions encountered within the body cavity. Situated just above the constriction provided by body 62 is an absorbent matrix 64 which may have a suitable nutrient therein, this matrix being held in the position shown in FIG. 5 as a result of the contraction of the flexible enclosure 60 by the body 62. Thus, the matrix 64 in the interior of the enclosure cannot move down beyond the constriction provided by the body 62 even though a tensioned springy member 66 fixed in any suitable way to the bottom end of the enclosure and to the matrix 64 tends to pull the latter downwardly. This springy member 66 may, if desired, be fixed directly to the wick 68 which is identical with any of the above wicks and which in this case is fixed to the matrix 64. The wick 68 carries the closure plug 70 at the exterior of the device, and the wick 68 extends through an opening 72 of the enclosure with a slight clearance or with practically no clearance.

With this device, after it has remained in the body cavity for a certain time interval, the conditions encountered in the body cavity such as temperature or the liquids therein will result in melting or dissolving of the body 62, respectively, so that as a result the enclosure can expand, thus releasing the matrix 64 together with the wick 68 to the force of the tension spring 66 which now retracts the wick to the condition shown in FIG. 6 where the plug 70 completely closes the enclosure. Thus, this embodiment also can achieve the results of the invention.

FIGS. 7 and 8 show a construction similar to that of FIGS. 5 and 6. The only difference is that in this case a compression spring 74 surrounds the wick between the top end of the enclosure 60 and the holding means 62 which responds to the conditions in the body cavity for releasing the container 60 so that it is capable of expanding as described above. The compression spring 74 urges the dry absorbent matrix 76 toward the constriction through which the matrix 76 cannot pass because the constriction is too small.

Thus, with this embodiment after the time interval necessary for the dissolving or melting of the holding means 62 has elapsed, the enclosure 60 will expand thus permitting the spring 74 to expand to place the parts in the condition shown in FIG. 8 according to which the plug 70 seals the opening 72 in the manner described above. With this embodiment it is possible to situate a suitable nutrient medium 78 in the enclosure at the side of the constriction opposite from the matrix 76. As a result when the spring 74 expands the matrix 76 will place the body fluids in engagement with the nutrient means 78, as shown in FIG. 8, and now it will be possible for the microorganisms to grow while the device remains in the body cavity without any danger of having an undesirable effect on the body.

The embodiment of the invention which is illustrated in FIG. 9 includes a transfer means 80 in the form of a wich which has at the exterior of the illustrated enclosure 82 a frayed end 84 capable of effectively absorbing body fluids. In this case the transfer means in the form of the wick extends through a slit 86 defined between springy lip portions of the enclosure 82. Thus, this enclosure may be made in the form of a pair of shells having exterior flanges joined together with these flanges not being joined where the slit 86 is provided so that they will form a slit while at the same time they tend to close upon themselves if the wick 80 is not present. At the end of the enclosure 82 opposite from the slit 86, the flanges are closed upon a tensioned springy member in the form of a rubber band 88, for example. This rubber band is connected to the inner end of the wick 80. This wick 80 is provided with an enlargement such as a knot 90 forming part of the wick itself, and this knot 90 engages a trigger ring 92 fixed in the interior of the enclosure. This trigger ring 92 may be in the form of a suitable ring of agar or gelatin or the like which has sufficient rigidity when dry to maintain the parts in the condition shown in FIG. 9 where the springy member 11 is tensioned. The trigger ring 92 is fixed by any suitable adhesive or the like in the interior of the enclosure or it may extend partly into an interior groove which is formed in the enclosure so as to remain fixed therein in this way.

The wick 80 may, for example, be made of nylon and may or may not contain a nutrient.

Thus, when the embodiment of FIG. 9 is introduced into a body cavity the frayed end 84 of the transfer means will effectively transfer fluid to the interior of the enclosure, and this fluid will travel along the wick 80 up to the knot 90 so as to be transferred by this enlargement into engagement with trigger ring 92. The fluid will cause the ring 92 to yield after a certain time interval, with the result that the spring 88 will not retract the entire wick 80 into the interior of the enclosure with the slit 86 closing upon itself.

In this case it is possible to inspect the wick itself to determine whether or not microorganisms have grown, in the event that the nutrient is provided in the wick itself.

The embodiment of FIG. 10 is substantially similar to that of FIG. 9. The difference is that instead of a ring of agar or gelatin to form the trigger 92, a gelatin shell 94 is pressed into the container 82 and maintained therein in the position shown in FIG. 10 by any suitable adhesive. The part of the wick 80 which engages the trigger shell 94 made of gelatin is provided with a frayed portion 96 for distributing the fluid effectively over the gelatin shell 94 so as to effectively dissolve the latter. Thus, in this case when the shell 94 dissolves the tensioned springy member 88 will contract to draw the wick 80 into the interior of the enclosure 82 which has a slit 86 which closes upon itself as described above in connection with FIG. 9, when the wick is entirely withdrawn into the enclosure.

However, in this case the wick may carry a body 98 of a suitable dry medium provided with a suitable nutrient for growing microorganisms at this body 98. Of course this body 98 is only dry initially. It will absorb the body fluid to encourage the growth of microorganisms.

Alternatively or together with the body 82 it is possible to provide at the wick an enlargement in the form of a knot 100 or the like for the purpose also of growing microorganisms at this enlargement.

By way of these procedures, namely utilizing elements 100 or 98 it is possible to concentrate the microorganisms at the location where these enlargements are located for the purpose of greatly enhancing the visibility of the microorganisms.

It has been found that at the junction between the wick and an enlargement such as a knot 100 or a body 98, or even a sponge or other matrix, there will be a certain retarding of the flow of the fluid and in particular the more viscous portions thereof will tend to collect at the junction between the wick and the enlargement, so that it is precisely at this region that the microorganisms are most highly concentrated so as to become most visible at this region. Thus it would be in particular to this region that a dye will be provided by way of a suitable syringe the needle of which is pierced through the clear plastic enclosure into engagement with the area where the microorganisms have grown.

As a further feature, it is highly desirable to provide the medium which carries the nutrient, particularly at is location where it engages the wick and where any microorganisms are thus concentrated as pointed out above, with a clear transparent structure for optically enhancing the visibility. For example, it is possible to use microspheres or to use clear transparent strands for the wick in such a way that the wick will be visible not only at the surface which one looks at but also completely through and behind at the opposed surface thereof so that with such a construction the visibility of the microorganisms is optically enhanced. In the case where the absorbent medium includes microspheres, for example, the microorganisms may grow all over these microspheres which because of their clear transparency provides an optical enhancing of the visibility of the microorganisms in the manner describe above.

Of course, any of the above devices of the invention can be carried at least partly by a body of soft material such as cotton wadding, sponge rubber, or the like, which will serve not only the purpose of comfortably positioning devices of the above type, if necessary, in a body cavity but also in some cases the purpose of absorbing fluids which reach the devices of the invention through such a body.

What is claimed is:

1. In a device for collecting body fluids and/or detecting whether or not certain microorganisms are present in a body cavity, an enclosure having a hollow interior and adapted to be introduced into the body cavity, transfer means extending through a wall portion of said enclosure from the exterior to the interior thereof for automatically transferring a body fluid from the exterior to the interior of said enclosure in response to contact of said transfer means with a body fluid in the body cavity, and closure means formed at least in part by a portion of said enclosure for closing said enclosure automatically, after transfer of a body fluid into said enclosure by said transfer means, in a manner preventing body fluids and/or microorganisms therein from moving into or out of said enclosure after closure of the latter by said closure means, said closure means including a means for automatically rendering said closure means operable to close said enclosure, so that the transfer of the body fluid from the exterior to the interior of said enclosure and the closing of said enclosure go forward in a fully automatic manner upon introduction of said enclosure into the body cavity.

2. The combination of claim 1 and wherein said transfer means is a capillary transfer means which acts by capillary action for transferring a body fluid from the exterior to the interior of said enclosure.

3. The combination of claim 2 and wherein said transfer means is an elongated wick extending from the exterior to the interior of said enclosure.

4. The combination of claim 3 and wherein said closure means includes a plug carried by said wick at an outer free end thereof situated at the exterior of said enclosure, the latter being formed only with an opening through which said wick extends, and said closure means further including a retracting means in sad enclosure acting on said wick for retracting the latter into the interior of said enclosure, after collecting of body fluids therein, to an extent sufficient for closing said opening with said plug.

5. The combination of claim 4 and wherein said retracting means including a tensioned springy member in said enclosure connected with said wick for retracting the latter to place said plug in a position closing said opening, and said closure means further including a trigger means in said enclosure for responding to transfer of fluid by said wick from the exterior to the interior of said enclosure for automatically releasing said tensioned springy member to retract said wick.

6. The combination of claim 5 and wherein said enclosure is flexible and springy while said trigger means includes a means initially holding said enclosure in a compressed condition and responding to conditions in the body cavity for releasing said enclosure to expand with said expansion of said enclosure resulting in release of said tensioned springy member to retract said wick.

7. The combination of claim 1 and wherein said closure means includes a wall portion of said enclosure through which said transfer means extends with said wall portion having the capability of automatically closing upon itself in a fluid-tight manner when said transfer means does not extend therethrough, said closure means further including a retracting means for automatically retracting said transfer means entirely into the interior of said enclosure, whereupon said wall portion will automatically close upon itself for completely closing said enclosure.

8. The combination of claim 7 and wherein said transfer means is a wick while said closure means has a wall portion formed with a slit through which said wick extends and which closes upon itself when the wick does not extend through said slit of said wall portion, a springy member acting on said wick to tend to retract the latter into said enclosure, said wick carrying an enlargement in the interior of said enclosure and the latter having in engagement with said enlargement a means which will respond to transfer of fluid from said enlargement to the latter means for releasing said enlargement and thus releasing said wick to the force of said springy member to be retracted entirely into said enclosure.

9. The combination of claim 1 and wherein a means is situated in said enclosure for placing a nutrient in contact with microorganisms in the body fluid transferred into said enclosure for growing said microorganisms in the interior of said enclosure after the latter is closed by said closure means.

10. The combination of claim 9 and wherein said means for placing said nutrient in contact with microorganisms is formed by a part of said transfer means itself which carries a suitable nutrient.

11. The combination of claim 10 and wherein said means for placing said nutrient in contact with the micro-organisms forms with said transfer means a junction where the body fluid with microorganisms, if any, therein collects for rendering the microorganisms clearly visible at said junction.

12. The combination of claim 10 and wherein said enclosure is transparent and capable of being treated for placing a dye in engagement with organisms which have grown in said enclosure to render said organisms readily visible.

13. The combination of claim 1 and wherein a nutrient means is situated in said closure for receiving microorganisms and growing the same in said enclosure after the latter is closed by said closure means, said nutrient means being carried in said enclosure by a transparent optically clear structure which optically enhances the visibility of microorganisms.

14. The combination of claim 1 and wherein a preservative means is situated in said enclosure for preserving body fluid collected therein.

* * * * *